United States Patent
Miclaus

(10) Patent No.: US 10,842,503 B1
(45) Date of Patent: Nov. 24, 2020

(54) HANDS-FREE INFLATABLE TOURNIQUET

(71) Applicant: Geta V. Miclaus, Santa Ana, CA (US)

(72) Inventor: Geta V. Miclaus, Santa Ana, CA (US)

( * ) Notice: Subject to any disclaimer, the term of this patent is extended or adjusted under 35 U.S.C. 154(b) by 131 days.

(21) Appl. No.: 15/956,882

(22) Filed: Apr. 19, 2018

(51) Int. Cl.
*A61B 17/135* (2006.01)
*A61B 17/132* (2006.01)

(52) U.S. Cl.
CPC ........ *A61B 17/135* (2013.01); *A61B 17/1322* (2013.01)

(58) Field of Classification Search
CPC . A61B 17/132; A61B 17/1322; A61B 17/135; A61B 17/1325; A61B 17/1355; A61B 17/1327
See application file for complete search history.

(56) References Cited

U.S. PATENT DOCUMENTS

| | | | | |
|---|---|---|---|---|
| 6,007,559 A | * | 12/1999 | Arkans | A61B 17/135 601/150 |
| 9,750,895 B1 | * | 9/2017 | Alsaifi | A61M 5/427 |
| 2009/0155341 A1 | * | 6/2009 | Gavriely | A61L 27/34 424/445 |
| 2010/0078088 A1 | * | 4/2010 | Navarro | A41G 5/02 137/565.12 |
| 2012/0330112 A1 | * | 12/2012 | Lamego | G06F 19/00 600/301 |
| 2013/0340767 A1 | | 12/2013 | Biddex et al. | |

* cited by examiner

*Primary Examiner* — Majid Jamialahmadi
(74) *Attorney, Agent, or Firm* — Sanchelima & Associates, P.A.; Christian Sanchelima; Jesus Sanchelima

(57) ABSTRACT

The present invention provides a tourniquet apparatus that can be inflated hands-free. The tourniquet apparatus includes a sleeve and a pressurizing device to provide pressurized air to inflate the sleeve as required. In the tourniquet apparatus, the pressurizing device includes a pedal that is foot-operated and can be used to regulate the flow of pressurized air therein.

12 Claims, 2 Drawing Sheets

HANDS-FREE INFLATABLE TOURNIQUET

BACKGROUND OF THE INVENTION

1. Field of the Invention

The present disclosure generally relates to a tourniquet apparatus; and more particularly to a tourniquet apparatus that can be inflated hands-free by a single clinician during a medical procedure.

2. Description of the Related Art

During limb surgeries, be it orthopedic or plastic surgeries, it is highly desirable to provide a bloodless field to decrease the surgical and anesthetic risk to the patient. Surgical tourniquets are used to prevent blood flow to a limb and enable surgeons to work in a bloodless operative field. This allows surgical procedures to be performed with improved precision, safety and speed. There are a number of different varieties of tourniquets, the simplest one being a flexible tube which is tightly secured around the limb, e.g., to occlude arterial blood flow. Presently, pneumatic tourniquets have been widely adopted which use a compressed gas source to inflate a cylindrical bladder in order to compress the underlying blood vessels.

One of the many medical applications of a tourniquet includes, using a tourniquet for dilating a vein in an appendage for inserting a peripherally inserted central venous catheter. Virtually, it should be possible to insert central catheters, such as peripherally inserted central catheters, by a single personnel, and does not really require a team for the purpose. However, in practical scenarios, the insertion personnel, for example the clinician/surgeon, have to usually juggle between many items and perform many steps, like inflating and regulating the pressure of the tourniquet with his/her hands constantly which may necessitate the need of help from other personnel due to the complexity of the conventional tourniquet equipment.

US Patent Publication No. 20130340767 A1 discloses a spring biased tourniquet that can be placed on the exterior of a patient's appendage, such as on his or her arm. The spring tourniquet will exert pressure on the appendage to constrict and artery or dilate vein. Terminal ends of the spring member can be pulled apart to either reduce pressure or to disengage the patient's appendage. This spring biased tourniquet is especially suited for use in a peripherally inserted central catheter (PICC) procedure where the tourniquet can be placed on the exterior of a surgical drape, where it remains visible, and pressure can be reduced to avoid thrombosis without compromising the sterile barrier is surrounding the patient during this procedure. Although, such spring biased tourniquet may be relatively simple to apply; however, it does not provide any hands-free means for controlling the pressure exerted by the tourniquet on the patient's appendage.

Other documents describing the closest subject matter provide for a number of more or less complicated features that fail to solve the problem in a convenient and efficient manner. None of these documents suggest the novel features of the present invention.

SUMMARY OF THE INVENTION

It is one of the main objectives of the present invention to provide a tourniquet apparatus which can be inflated hands-free.

It is another objective of the present invention to provide a tourniquet apparatus in which the pressure in a sleeve can be regulated easily.

It is yet another objective of the present invention to provide a tourniquet apparatus which is simple to apply to a patient's appendage.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Illustrative embodiments of the present invention are described below. The following explanation provides specific details for a thorough understanding of and enabling description for these embodiments. One skilled in the art will understand that the invention may be practiced without such details. In some instances, well-known structures, processes and functions have not been shown or described in detail to avoid unnecessarily obscuring the description of the embodiments.

It shall be noted that unless the context clearly requires otherwise, throughout the description, the words "comprise," "comprising," "include," "including," and the like are to be construed in an inclusive sense as opposed to an exclusive or exhaustive sense; that is to say, in the sense of "including, but not limited to." Words using the singular or plural number also include the plural or singular number, respectively while adhering to the concepts of the present invention. Furthermore, references to "one embodiment" and "an embodiment" are not intended to be interpreted as excluding the existence of is additional embodiments that also incorporate the recited features.

Figure 1:
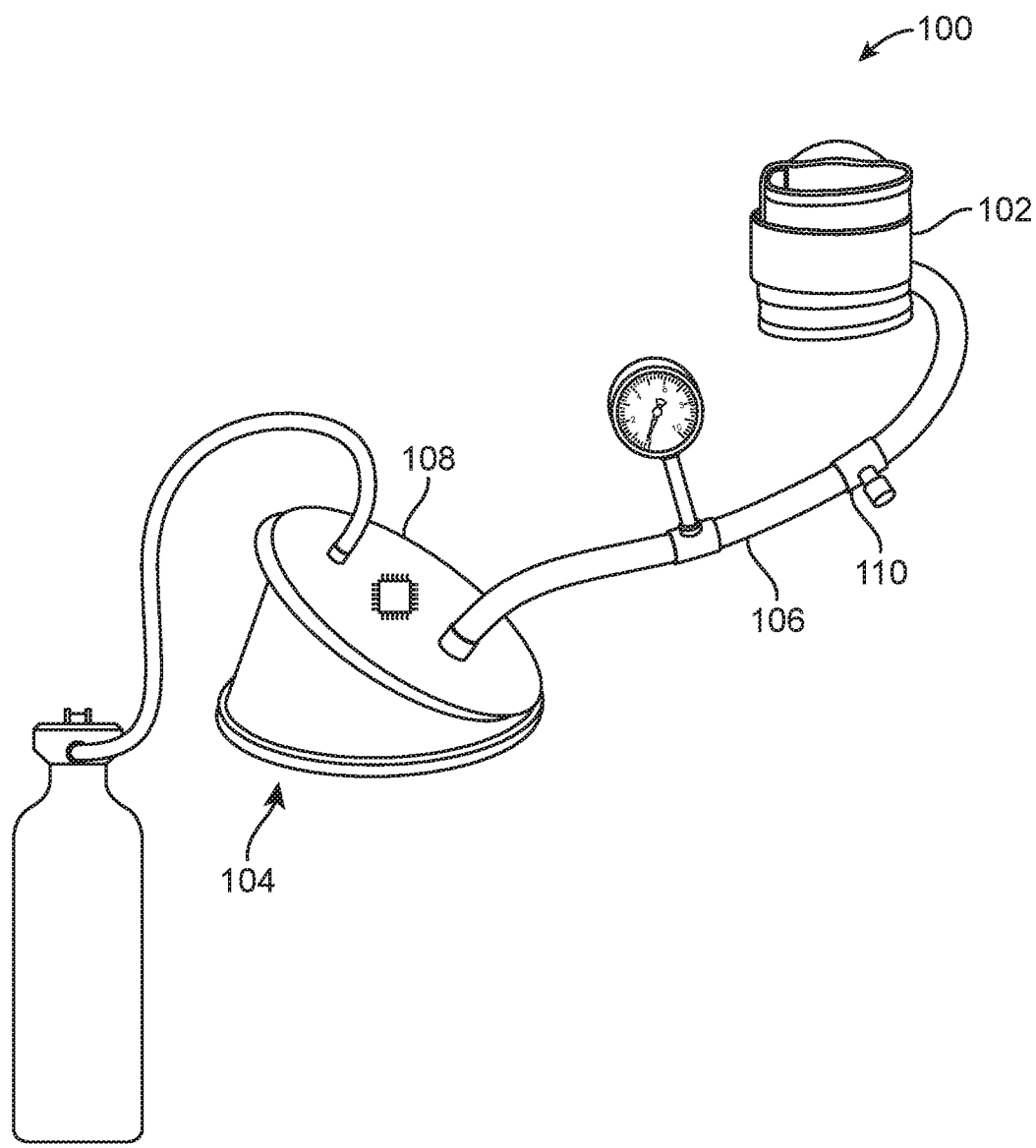
FIG. 1 illustrates a diagrammatic perspective view of a tourniquet apparatus, in accordance with one or more embodiments of the present disclosure.
Figure 2:
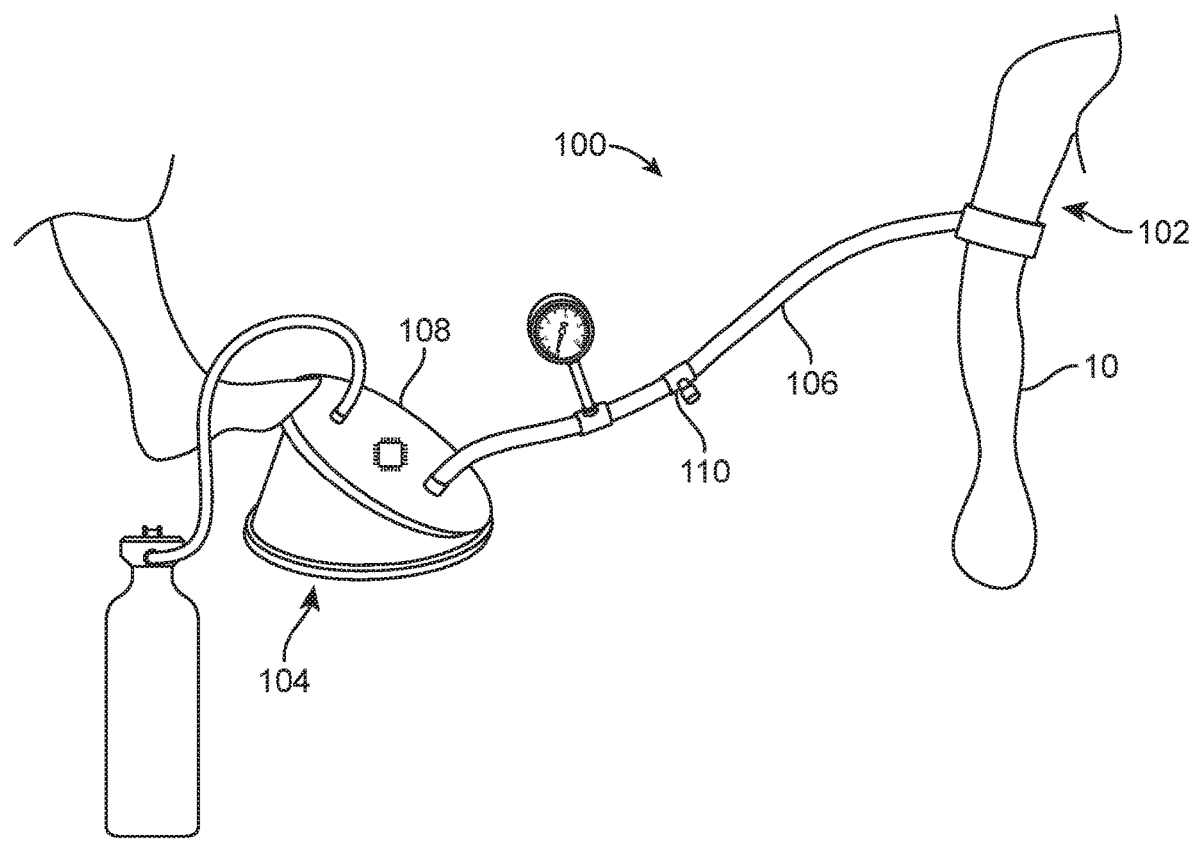
FIG. 2 illustrates the tourniquet apparatus of FIG. 1 being used with a patient's appendage, in accordance with one or more embodiments of the present disclosure.

Referring to the drawings, FIG. 1 illustrates a diagrammatic perspective view of a tourniquet apparatus (hereinafter referred to by the numeral 100), in accordance with an embodiment of the present disclosure. FIG. 2 illustrates the tourniquet apparatus 100 being used with an appendage 10, represented as a human arm. It may be understood that although the appendage 10 has been shown as an arm, the appendage 10 could be any other limb, such as, but not limited to, leg, thumb, finger or toe, without affecting the scope of the present disclosure. Additionally, the present tourniquet apparatus 100 may be universally configured for use with both the left arm or right side appendages. In embodiments of the present disclosure, the tourniquet apparatus 100 is an inflatable tourniquet in which the pressure applied to the appendage may be varied before or during the surgical or medical procedure, as discussed in the subsequent paragraphs.

In an embodiment, the tourniquet apparatus 100 may generally include a sleeve 102, and a pressurizing device 104 connected to the sleeve 102 via a tube 106. In particular, the sleeve 102 may be disposed in fluid communication with the pressurizing device 104, via the tube 106. In the present tourniquet apparatus 100, the pressurizing device 104 may be a foot-operated device. In an embodiment, as illustrated in the accompanied drawings, the pressurizing device 104 may be a foot-pump which may be operated by providing reciprocating force to generate pressurized air (e.g., like foot-operated bicycle pump) to supply the pressurized air to the sleeve 102, for inflating the sleeve 102 as required. In other alternate examples, the pressurizing device 104 may include a compressed air source seen in the figures and a foot-operated valve (not shown) connected to the compressed air source to regulate the flow of pressurized air therefrom to the sleeve 102. In yet other examples, the pressurizing device 104 may include electric pump, $CO_2$ inflators, voice is command based inflators (e.g., using smart-assistant like Amazon Alexa™), or the like, without any limitations.

As illustrated in FIG. 1, the pressurizing device 104, in the form of a foot pump, may include a pedal 108 onto which the personnel may provide the reciprocating force for generating pressurized air. Reciprocating foot pumps for such purposes are known and are commonly designed with two generally flat plates joined by a single hinge about which the plates can be turned in a reciprocating fashion by acting on the ends remote from the hinge. In each case the volume between the plates is enclosed by a flexible membrane to define a chamber, and respective unidirectional valves allow air in and out of the chamber as it is expanded and compressed by the reciprocating motion.

In an embodiment, the sleeve 102 is designed in the form of a cuff like structure. Generally, the sleeve 102 may have closure mechanisms such as snaps, Velcro®, and the like for securing it around the appendage 10. In one example, the sleeve 102 may be made of a thermoplastic polyurethane elastomer rubber, such as thermoplastic polyurethanes (TPU), nylon, etc. Such material may be chosen to provide a high wear resistance, high oil resistance, good elasticity and other similar properties. Also, the sleeve 102 made of nylon may be made disposable for sterilization and sanitation purposes. In some examples, the inner surface of the sleeve 102 may be coated with a silica gel layer to absorb moisture, from sweat or the like, and further for preventing air to permeate through thereof. Further, the sleeve 102 may be easier to bend and contact with the skin surface of the appendage 10 without wrinkles, thereby enhancing the hemostatic effect.

In the tourniquet apparatus 100, the tube 106 may be a flexible tube which may easily dispose the sleeve 102 in fluid communication with the pressurizing device 104. In one example, the tube 106 may be corrugated tube with specification suitable for the purpose described herein. Further, in one embodiment, the tourniquet apparatus 100 may include a release valve 110 provided on the tube 106. The release valve 110 may allow to release the pressurized air from the sleeve 102 to the atmosphere, for deflating the sleeve 102 in the tourniquet apparatus 100 as required. In one example, the release valve 110 may be provided on the tube 106 in proximal to the sleeve 102 for easily releasing the pressure inside the sleeve 102; however, such arrangement shall not be construed as limiting to the present disclosure. The release valve 110 may be operated by any means known in the art.

In some other examples, the pressurizing device 104 may be used to release the pressurized air from the sleeve 102, via a second tube (not shown) connected to the sleeve 102, thereby deflating the sleeve 102 as required. For example, when the personnel desires to inflate the sleeve 102, the personnel may put his/her foot on a first side of the pedal 108 to open a valve (not shown) fluidly connecting the compressed air source to the sleeve 102 therein and thereby allow the pressurized air to travel to the sleeve 102, for inflating the sleeve 102. Similarly, when the personnel desires to deflate the sleeve 102, the personnel may put his/her foot on a second side of the pedal 108 to open a release valve (not shown) therein and thereby allow the pressurized air to escape to the atmosphere from the sleeve 102, for deflating the sleeve 102. In other alternate examples, the pedal 108 may be used for controlling the release valve 110 as well; thus, making the deflation process of the sleeve 102 also possibly hands-free.

In some examples, the pressurizing device 104 may be provided with a pressure measuring instrument, such as a pressure gauge, a barometer, etc. Such instrument enables the personnel to measure the current pressure and accordingly regulate the pressure being used for inflation of the sleeve 102, thus minimizing the risk of using less or excessive pressure. Again, in some examples, the pressurizing device 104 may be provided with a microcontroller seen in the figures to maintain pressure of the sleeve 102 around the appendage 10 at a minimum acceptable level and thereby minimizes nerve damage caused by the compression of the tourniquet on nerve tissues over long periods. The microcontroller may further be configured to be responsive to changes in the blood pressure measured by a pressure monitor to operate the tourniquet apparatus 100 to maintain the pressure about the appendage 10 at a level greater than the patient's blood pressure by a predetermined amount.

As noted earlier, keeping a tourniquet on for a longer period of time may start damaging the veins, and may also affect the ultrasound to be carried on the appendage 10 because it will gray out and become blurry. The tourniquet apparatus 100 of the present disclosure with convenient foot-operated pressurizing device 104 may help to circumvent most of these complications during a medical procedure. The tourniquet apparatus 100 of the present disclosure may particularly be useful for inserting a central catheter. A central catheter is a catheter that is placed into a large vein through which medical professionals may repeatedly deliver fluids or medications to a patient. Central catheters can also be used to withdraw fluids, such as blood, for testing. Central catheters can be inserted into various parts of the patient, but are generally inserted in veins in the neck. Central catheters inserted into arms are known as peripherally inserted central catheters, or "PICC line." PICC line may be placed in a patient's arm to allow prolonged intravenous access, such as for is extended antibiotic treatment, chemotherapy, and so forth.

Typically, a team of two or more personnel are required to complete insertion of PICC line since during PICC line insertion, such tourniquet is applied before the personnel has applied the sterile drape over the patient's body and has put on the sterile gown and gloves, because of which the personnel cannot touch the tourniquet unless there is another clinician who is available to tie the tourniquet. However, in the present tourniquet apparatus 100, since the pressurizing device 104 is foot-operated, the personnel may focus his/her hands on carrying out the primary medical procedure while carrying out regulation of the pressure via his/her foot. Thus, the present tourniquet apparatus 100 could possibly eliminate the need of having a team of personnel required for simple procedure of inserting PICC line, and may enable a single personnel to carry out the task without much complications.

Furthermore, the present tourniquet apparatus 100 also ensures that the pressure to dilate the vein is applied for the shortest time possible, and, generally, the lowest possible pressure which is needed to visualize the vein using the ultrasound is applied. Thus, the present tourniquet apparatus 100 will help to keep the vein(s) healthy (called vein preservation), and avoid any possible permanent vein damage (by rupturing the fragile veins walls). The present tourniquet apparatus 100 further avoids the risk of creating of blood clots (thrombosis) due to occlusion applied for extended time.

The hands-free utilization of the tourniquet apparatus 100 will allow a single clinician' personnel to compress a vein during needle accessing while placing a PICC line, using a foot operated pressurizing device 104 therein. This technique will enable the personnel to keep his/her both hands focused on the medical procedure, rather than to regulate the pressure, and thus may shorten is the time for medical procedure, which in turn may reduce a number of complications associated therewith. It may be understood that, in some examples (as noted earlier), both inflation and deflation of the sleeve 102 may be carried out using the foot operated device itself. In the present examples, the design of the tourniquet apparatus 100 may also help with securing a surgical drape (not shown) in proper position during a surgical procedure, thus helping with the sanitization and disinfection during the procedure. It may be understood that the tourniquet apparatus 100 is not limited to the common practice of attending to a wound or to use with a PICC line as herein described in detail, and may be applicable to be used with any other medical procedure requiring the use of tourniquet without any limitations.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A hands-free inflatable tourniquet, comprising:
a sleeve, a pressurizing device disposed in fluid communication with said sleeve through a tube, a compressed air source supplying said pressurizing device with compressed air, and a valve regulating the flow of said compressed air, wherein said pressurizing device is a foot operated device, wherein said pressurizing device includes a pedal to actuate said foot-operated device, wherein said pedal includes two flat plates hingedly joined together such that said two flat plates can be turned in a reciprocating fashion, wherein a volume between said two plates is enclosed by a flexible membrane to define a chamber, wherein said chamber is expanded and compressed in response to a reciprocating motion applied to said pedal, wherein said two flat plates includes a top plate and a bottom plate, wherein said top plate is slanted with respect to said bottom plate, said tube is mounted to said top plate of said pedal.

2. The hands-free inflatable tourniquet of claim 1 wherein said sleeve includes an inner surface coated with a silica gel.

3. The hands-free inflatable tourniquet of claim 1 wherein said tube is flexible.

4. The hands-free inflatable tourniquet of claim 1 wherein said pressurizing device includes a pressure measuring instrument.

5. The hands-free inflatable tourniquet of claim 4 wherein said pressure measuring instrument is a barometer.

6. The hands-free inflatable tourniquet of claim 1 wherein said pressurizing device includes a microcontroller adapted to maintain pressure of the sleeve around an appendage.

7. The hands-free inflatable tourniquet of claim 1 wherein said sleeve includes fasteners adapted to secure said tourniquet around a user's appendage.

8. The hands-free inflatable tourniquet of claim 7 wherein said fasteners are snap buttons, hook and loop fasteners, or magnets.

9. The hands-free inflatable tourniquet of claim 1 wherein said sleeve is made of a thermoplastic polyurethane elastomer rubber.

10. The hands-free inflatable tourniquet of claim 1 wherein said two flat plates are circular plates.

11. The hands-free inflatable tourniquet of claim 1 wherein said valve is a release valve located on said tube.

12. A hands-free inflatable tourniquet, consisting of:
a) a pressurizing device being a foot-operated device, wherein said pressurizing device includes a foot pedal, wherein said foot pedal includes two flat plates, wherein said two flat plates are a top plate and a bottom plate, wherein said top plate is hingedly attached to said bottom plate, wherein said top plate is angled with respect to said bottom plate, a flexible membrane disposed between a volume of said top plate and said bottom plate to define a chamber, wherein said foot pedal is expanded and compressed in response to a reciprocating motion, wherein said pressurizing device further includes a compressed air source connected to said pedal, a tube mounted to said top plate of said pedal, said tube further including a release valve, said pressurizing device further including a microcontroller and a pressure measuring instrument; and
b) a sleeve adapted to be mounted to a user's arm, wherein said sleeve is in fluid communication with said pressurizing device through said tube, wherein said sleeve is a cuff structure, wherein said sleeve is made of a thermoplastic polyurethane elastomer rubber adapted to provide high wear resistance, wherein said sleeve is coated with a silica gel layer adapted to absorb moisture, wherein said microcontroller is adapted to maintain a pressure of said sleeve around said user's arm.

* * * * *